United States Patent [19]

Serra

[11] Patent Number: 5,308,582

[45] Date of Patent: May 3, 1994

[54] SYRINGE CAPPING AND UNCAPPING DEVICE

[76] Inventor: Louis M. Serra, 5599 Cardinal Dr., Mentor, Ohio 44060

[21] Appl. No.: 16,695

[22] Filed: Feb. 11, 1993

[51] Int. Cl.⁵ ............................................. B01L 3/00
[52] U.S. Cl. .................................... 422/99; 294/116; 269/239; 269/254 CS
[58] Field of Search .............. 294/116; 604/192, 110, 604/187; 269/239, 254 CS; 422/99

[56] References Cited

U.S. PATENT DOCUMENTS

| | | | |
|---|---|---|---|
| 4,121,868 | 10/1978 | Pierce et al. | 294/116 |
| 4,169,621 | 10/1979 | McGill | 294/116 |
| 4,737,149 | 4/1988 | Gillilan | 604/192 |
| 4,742,910 | 5/1988 | Staebler | 206/365 |
| 4,846,803 | 7/1989 | Emerson | 604/192 |
| 4,878,705 | 11/1989 | Arnsquist | 294/116 |
| 4,955,865 | 9/1990 | Steiner et al. | 604/192 |
| 4,979,945 | 12/1990 | Wade et al. | 604/192 |
| 4,981,476 | 1/1991 | Aichlmayr et al. | 604/192 |
| 5,013,299 | 5/1991 | Clark | 604/114 |
| 5,024,666 | 6/1991 | Pituch | 604/263 |
| 5,078,695 | 1/1992 | Farrar, Jr. et al. | 604/192 |
| 5,078,696 | 1/1992 | Nedbaluk | 604/192 |

Primary Examiner—James C. Housel
Assistant Examiner—Lien Tran
Attorney, Agent, or Firm—Louis J. Weisz

[57] ABSTRACT

A hypodermic syringe uncapping device includes a housing enclosing two opposed, pivotal arms adapted to grip a cap protecting a hypodermic syringe needle. Upon insertion through a hole in the housing, the capped needle is forced against a movable plunger whose lower end engages one of a number of pins extending from the surface of a rotatable cam located between the arms. Rotation of the cam thus induced allows the arms to pivot toward each other under the urging of an arm-connecting spring, causing the arms to grasp the cap and thereby allow subsequent withdrawal of the needle. When the needle is reinserted in the cap and the cap is again pushed against the plunger, the cam is rotated still further, forcing the arms apart and permitting the cap to be withdrawn from the device.

16 Claims, 3 Drawing Sheets

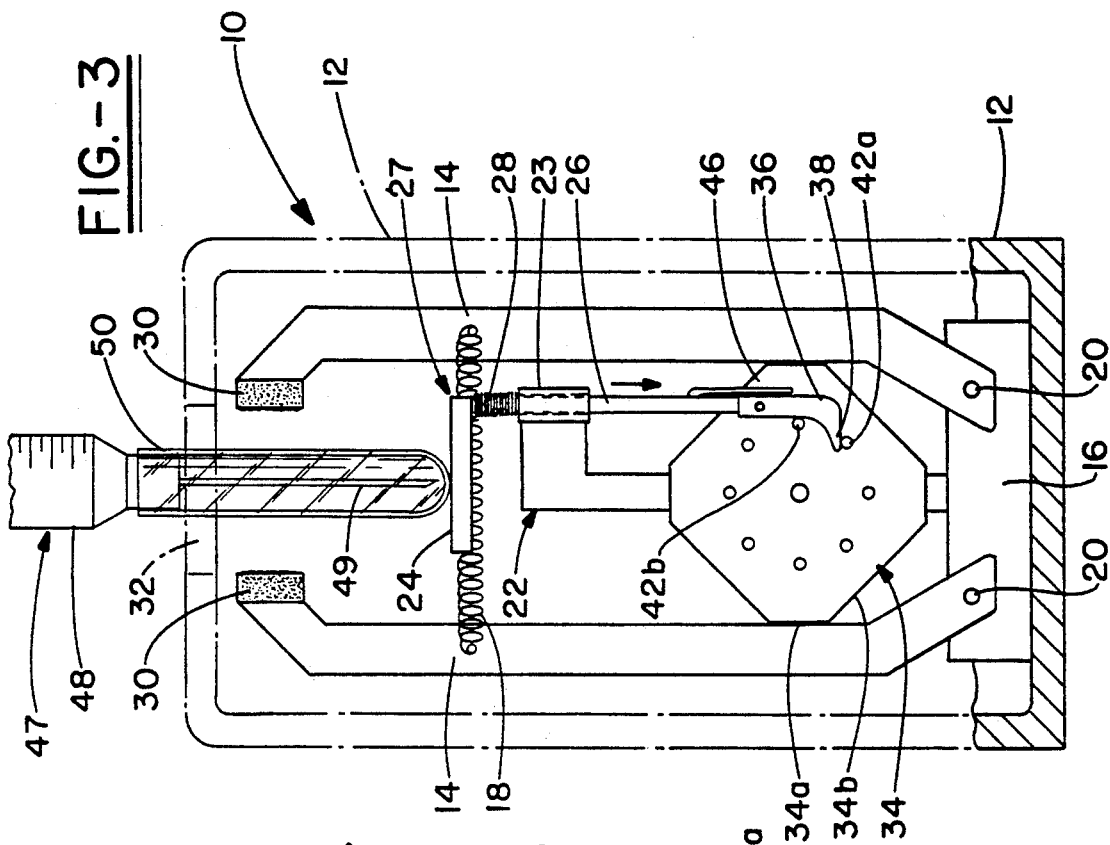
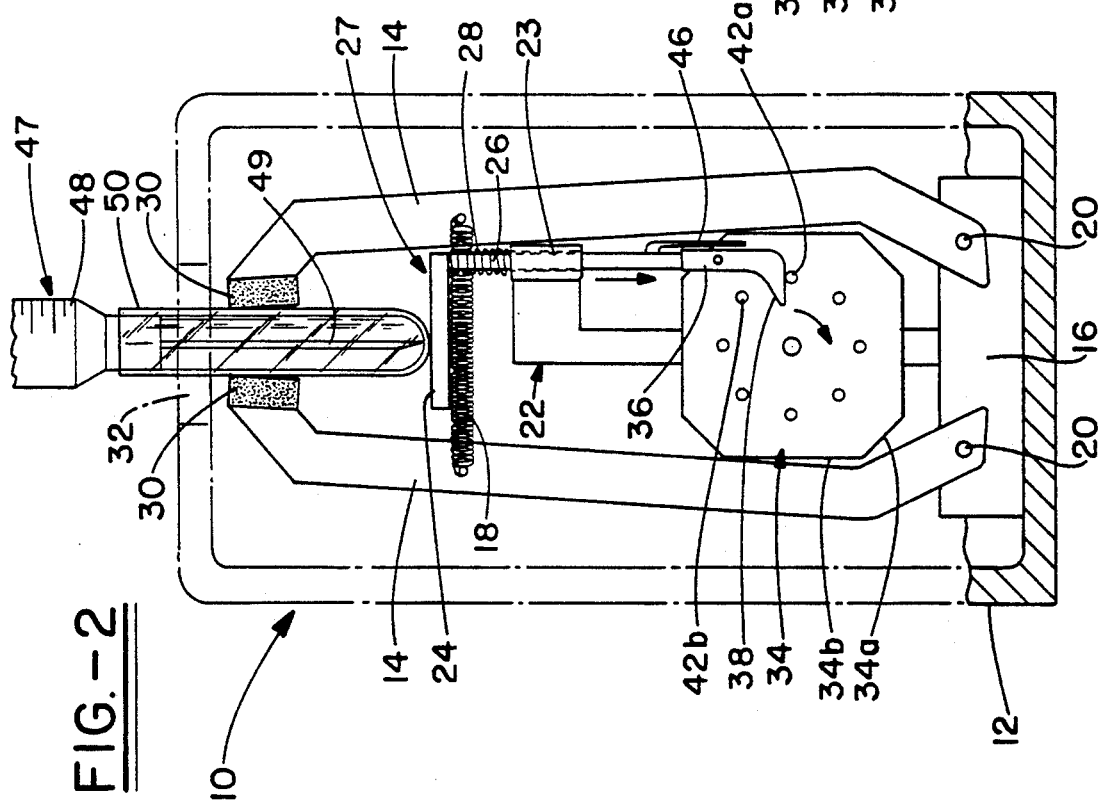

SYRINGE CAPPING AND UNCAPPING DEVICE

TECHNICAL FIELD

This invention relates to a device for improving the handling safety associated with the manipulation of hypodermic syringes. More particularly, this invention relates to the avoidance of accidental skin punctures or needle sticks by hypodermic needles during the capping and uncapping procedures required in connection with their use.

BACKGROUND OF THE INVENTION

Hypodermic syringes are commonly employed in a wide variety of medical operations, including those involving the withdrawal of blood from patients for diagnostic purposes; during the administration of patient medications, and for similar and other purposes. In the course of these activities, it is frequently necessary for medical personnel involved to operate the devices while simultaneously engaging in other activities, also requiring manual procedures. In such instances, it is obligatory, or often desirable to be able to operate a syringe with one hand. Inasmuch as hypodermic needles are normally enclosed with a cap or cover for protective reasons, it is necessary to remove the cap before use, and to replace it thereafter. While this is relatively easily accomplished when both hands are available for the task, it is difficult during times when only a single hand is available for the purpose.

Even in situations where both hands of an individual are free to operate the syringe, however, the capping and uncapping of hypodermic needles is not without significant hazards. In this regard, the risk to a medical practitioner as a consequence of the accidental transmittal of infectious pathogens due to accidental needle sticks following contamination of the hypodermic needle caused by its having previously been used in connection with an infected patient, or through other septic exposure, is a matter frequently having serious consequences.

In the latter regard, the increasing incidence of the invariably fatal Acquired Immune Deficiency Syndrome, as well as the risk of contracting hepatitis or other infectious diseases communicated, for example, through penetration of the skin by contaminated hypodermic needles emphasizes the importance of avoiding inadvertent needle sticks.

In the past, the advantages of procedures which permit "one-handed" capping and uncapping of hypodermic needles has been widely recognized and a variety of systems for providing this ability have been proposed.

U.S. Pat. No. 5,024,666, for example, discloses needle sheath gripping means operated by a solenoid consisting of plate-like members which shift from an aligned position to a misaligned position, causing the members to grip a needle protecting sheath in proximity therewith. However, while the device allows a hypodermic needle to be sheathed and unsheathed with one hand, it has the unfortunate disadvantage of requiring a source of electricity in order to function.

U.S. Pat. No. 5,013,299, on the other hand, comprises a base member with a plurality of sheath holders fastened therein, for instance by set screws. Although one-handed capping and uncapping is thus made possible, the use of the device requires that the sheaths be initially locked into the device, and to that extent it is relatively inconvenient.

U.S. Pat. No. 5,078,696 teaches a stand with a hollow stem into which a needle sheath can be inserted, being held therein by friction. The needle sheath is inserted until frictionally engaged in the stem, and withdrawn simply by overcoming the engagement friction through application of a withdrawal force. However, the device requires the use of specifically sized needle sheaths in order to be operable, and furthermore, the gripping friction may well not always work in the manner intended.

It is a first aspect of this invention, therefore, to provide a device for uncapping and capping hypodermic needles while minimizing the possibility of inadvertent needle stick mishaps therefrom.

A second aspect of this invention is to provide a device for making it safer to manipulate and use hypodermic syringes.

Another aspect of this invention is to minimize the spread of contagious diseases caused by accidents involving the use of contaminated hypodermic syringes.

A further aspect of this invention is to provide a device for capping and uncapping a hypodermic syringe that can be operated with only one hand.

An additional aspect of this invention is to provide a capping and uncapping device for hypodermic syringes which is able to accommodate needle caps of different diameters.

Still another aspect of this invention is to provide a device for capping and uncapping hypodermic syringes which does not require a source of electricity for its operability.

Yet another aspect of this invention is to provide a capping and uncapping device for hypodermic syringes, that is both uncomplicated and simple to operate.

Another aspect of this invention is to provide a capping and uncapping device for hypodermic syringes that can be easily cleaned and is autoclavable for sterile applications such as operating room use.

SUMMARY OF THE INVENTION

The foregoing and additional aspects of the invention are provided by a syringe uncapping device comprising two gripping arms for engaging a syringe needle cap. Gripping arm biasing means for biasing the gripping arms toward each other are also provided, as are camming means for positioning the gripping arms. The device includes activating means for adjusting the camming means, and the operative components are enclosed within a housing having an opening therein for inserting a hypodermic syringe needle cap.

The foregoing and still other aspects of the invention are provided by a syringe uncapping device comprising two opposed, pivotal gripping arms for engaging a syringe needle cap. A spring connects the two arms for biasing the same toward each other, while a rotatable cam plate is positioned between the arms. Rotation of the cam plate moves the arms alternately toward and away from each other, allowing the needle cap to be grasped or released, as desired.

The cam plate rotating means comprises a movable plunger shaft having two ends, a needle cap contact surface being located on one of the ends, while a cam-adjusting lever is pivotally attached to the other of the ends. Lever biasing means for urging the lever into alignment with the plunger shaft is also provided, as are mounting means through which the shaft passes, being slidable therein. The device further includes contact surface biasing means for urging the contact surface toward the opening. When pressure is applied to the contact surface by a needle cap inserted through the opening in the housing, the cam plate can be rotated to a first position where the arms grasp the needle cap, and when further pressure is applied by the needle cap, the cam plate is rotated to a second position where the needle cap is released from the arms.

BRIEF DESCRIPTION OF THE DRAWINGS

The invention will be better understood when reference is had to the following drawings, in which like-numbers refer to like-parts, and in which:

FIG. 2 is a cross-sectional view of the device of FIG. 1 with the needle cap inserted therein in a cap-grasping position;

FIG. 3 is a cross-sectional view of the device of FIG. 1 with the syringe further inserted into a cap-release position.

DETAILED DESCRIPTION OF THE INVENTION

Figure 1:
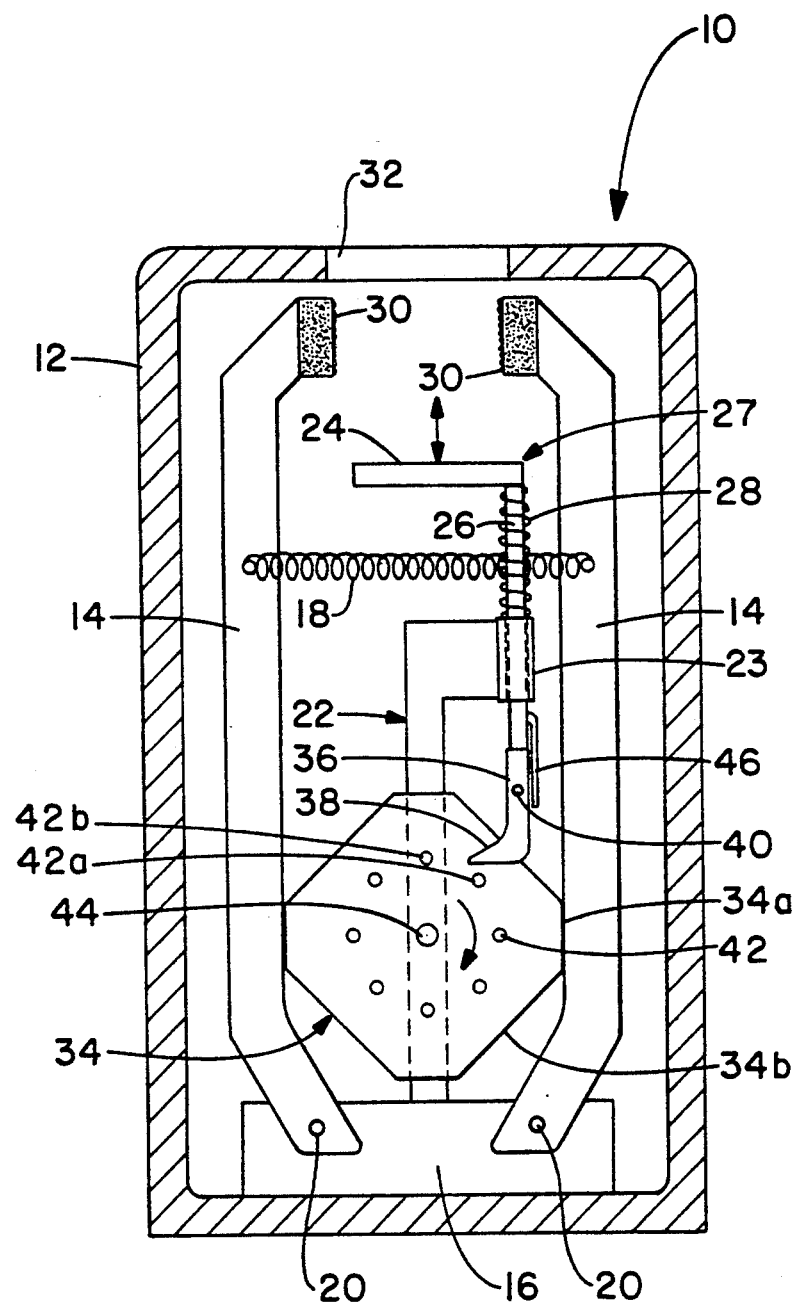
FIG. 1 is cross-sectional view of a device of the invention disposed to receive a hypodermic needle protective cap located therein.

FIG. 1 shows a cross-sectional view of the syringe uncapping device of the invention disposed to receive a hypodermic needle protective cap therein. As shown in the Figure, the device, generally 10, comprises a housing member 12 with an opening 32 located therein, the housing member being sufficiently large to accommodate whatever needle caps are likely to be encountered. Within housing 12 are located two opposed arms 14, being pivotal about arm pivot pins 20 attached to the arm-mounting base 16. While a solid base is shown on which both arms are mounted, individual attachment points can be provided if desirable or necessary. Optionally, the gripping portion of the arms 30 can have a toothed configuration, as shown, or rubber surfaces may be provided to enhance the gripping characteristics of the arms.

Mounted between the arms 14 on a yoke, generally 22, is a vertically rotatable 360° cam member, generally 34. As shown, the cam member has a plurality of pin-like projections 42 extending at right angles from the surface thereof in a pattern disposed about the pivot point 44. As illustrated in FIG. 1, the cam pivot point 44 is connected to yoke 22; however, the cam can be otherwise anchored if preferred. Yoke 22 is also fastened to the arm-mounting base 16, and the collar portion 23 of the yoke 22 is adapted to receive a plunger shaft 26 which forms part of the cam activating assembly, generally 27. The plunger shaft 26 is free to slide back and forth within yoke collar 23 and the plunger shaft is connected to a needle cap contact plate 24 at its upper end, while a cam operating level, generally 36, is pivotally attached to its lower end by pivot pin 40. An alignment spring 46 is also attached to the plunger shaft 26, the operation of the latter being described in further detail in the following. The plunger shaft 26 has a spring 28 disposed thereabout, and as stated, the shaft is free to slide through yoke collar 23 in either direction, as shown by the associated arrow. The proximity of arms 14 relative to each other is controlled by cam 34, which is designed to rotate in the direction of its associated arrow. Arm spring 18, fastened at either end to the arms, urges the arms toward each other to a degree controlled by the surfaces of cam 34.

As shown in FIG. 1, the cam consists of an octagonal plate, alternate sides having different lengths and being equal and parallel to the sides opposite them. Due to the different lengths of the sides, rotation of the cam 34 alternately causes the arms 14 to pivot either closer together, or further apart from each other in their outermost position, as shown in the Figure, the free ends of the arms 14 then, respectively, allowing the grasping, or the insertion or withdrawal of a needle cap into or out of the housing 12.

While an octagonally shaped cam is shown, other shapes may also be used, including an arcuate shape, providing the surface of the cam is so configured that the cam presents longer and shorter surface widths, alternately, with respect to the points of contact of the surfaces with arms 14.

The activating assembly 27 also includes an alignment spring 46, attached to plunger shaft 26, for the purpose of maintaining parallel alignment of cam operating level 36 with plunger shaft 26 as will be more fully explained in the succeeding. The cam operating lever also has an angled portion or lever "foot" 38 extending from the lower portion thereof, which will be more fully described in connection with FIG. 4.

FIG. 2 is a cross-sectional view of the device of FIG. 1 in which a needle cap has been inserted so as to cause the device to grasp the needle cap.

In the Figure, a capped hypodermic syringe, generally 47, has been inserted through opening 32, bringing the cap 50 into contact with contact plate 24. This forceful contact urges the plunger shaft 26 downward, guided by yoke collar 23 and against the urging of spring 28, causing the lever 36, particularly foot 38, into operating contact with cam rotator pin 42a.

The insertion pressure produces the clockwise rotation of cam 34, causing the longer cam peripheral surfaces 34b of the cam to come into engaging contact with arms 14. This permits spring 18 to urge the toothed portion 30 of the arms 14 toward each other into the cap-gripping position shown. In this condition, the cap is firmly held by the arms, and the syringe 48 with its associated needle 49 may be easily withdrawn from the grasped cap 50.

FIG. 3 is another cross-sectional view of the device of FIG. 1 in which the capped syringe has been further inserted into the syringe uncapping device, causing the release of the cap 50 as illustrated. In the Figure, the needle 49 of syringe 48 has been reinserted into needle cap 50, further force then being applied to the syringe 48, resulting in additional pressure being applied to contact plate 24. The further pressure on contact plate 24 causes additional downward travel of plunger shaft 26 through collar 23, the result being that operating lever 36, more particularly lever foot 38, moves cam rotating pin 42a so that the cam 34 is additionally rotated clockwise to a position where the shorter cam width surfaces 34a come into contact with arms 14, causing the arms to pivot outwardly and away from each other, releasing needle cap 50 and allowing it to be withdrawn from housing 12.

Figure 4:
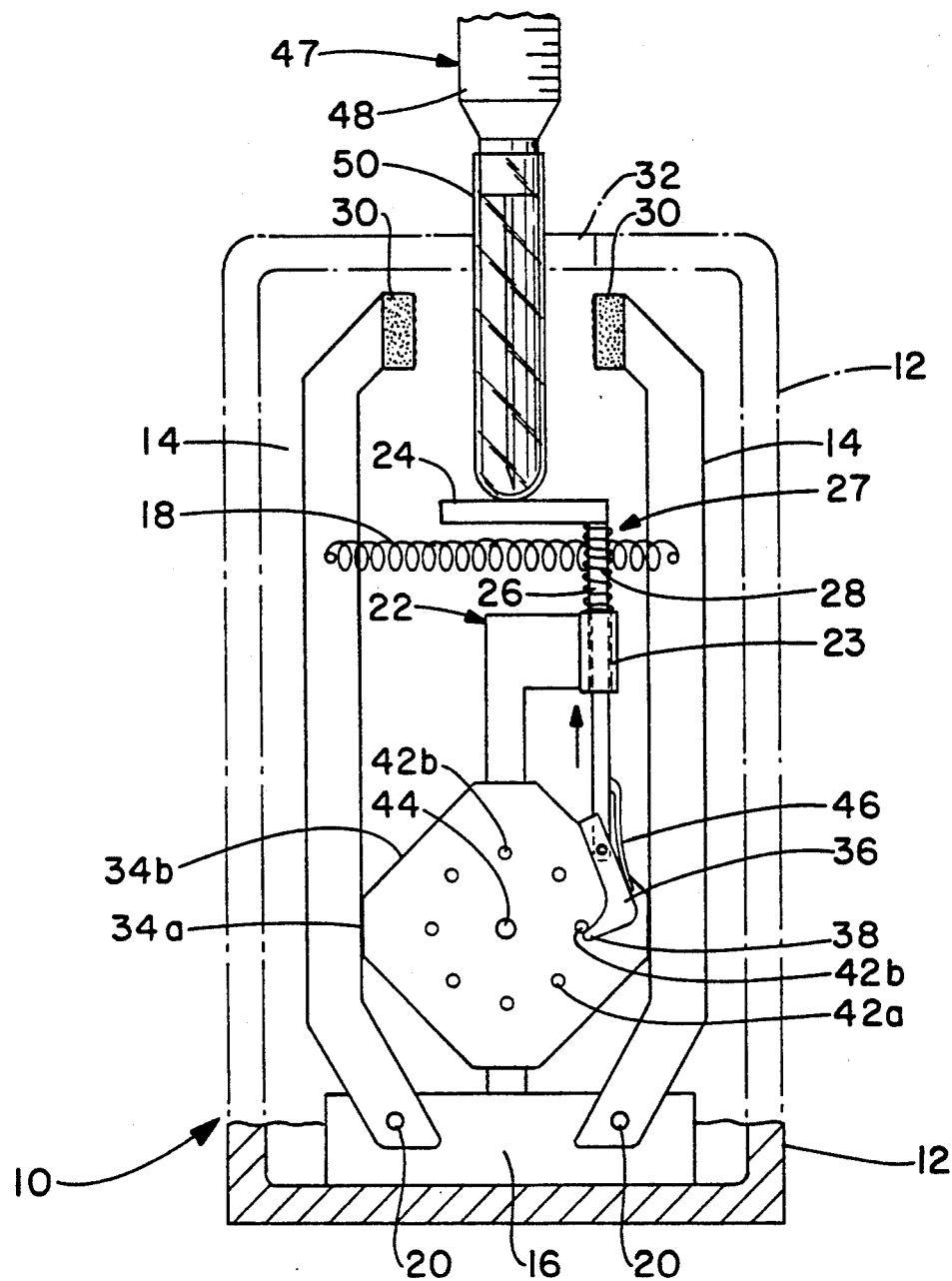
FIG. 4 is a cross-sectional view of the device of FIG. 1 during the withdrawal phase of the capped hypodermic needle syringe.

FIG. 4 is a cross-sectional view of the device of FIG. 1 showing the withdrawal of the capped hypodermic syringe. As the capped syringe 47 is withdrawn, the pressure is removed from needle cap contact plate 24, whereupon plunger spring 28 urges the needle cap contact plate upward. This movement causes the lever foot 38 of cam-operating lever 36 to encounter cam rotator pin 42b. At this point, the cam-operating lever 36 pivots about pivot pin 40, against the urging of alignment spring 46. After the lever foot 38 has proceeded upward and past cam rotator pin 42b, the alignment spring 46 urges the operating lever 36 back into an aligned position in which it again becomes parallel with plunger shaft 26. The device is then able to repeat the cycle described. The cam rotator pin 42b thereafter becomes the operating pin against which the cam operating lever 36 acts to cause a subsequently inserted needle cap to be grasped.

It can be seen that a slight angle in the upper surface of lever foot 38 facilitates the pivoting of the operating lever 36 in its return to the standby operating position. This angle may vary considerably, an angle of from about 20° to 70° normally being preferred.

The rotator pins 42 may conveniently simply comprise pins extending at right angles from the surface of cam 34, but may also take the form of projecting tabs or similar structure adapted to interact with cam-operating lever 36. The number of projections or pins will vary, depending upon the dimensions of the device; however, it has been found that about eight such structures are advantageously disposed on the cam surface, substantially as shown in the Figures.

While contact plate 24 is shown cantilevered from plunger shaft 26, the plate could alternatively be centered on the plunger shaft. Furthermore, although arm spring 18 is a convenient way in which to bias the arms 14 toward each other, a different arrangement, for example, the provision of separate springs for each of the arms shown could also be employed.

The dimensions of the device may be varied within broad limits, and will depend upon the environment in which the device is to be used, as well as the nature of the hypodermic syringes with which it is to be employed. The device should be constructed in such a way, however, that it is stable during the capping and uncapping process, a requirement addressed by attention both to the weight of the device, as well as the dimensions of its base member. Also to facilitate such stability, the device can be furnished with attachment means on its base, for example, double-sided adhesive; magnetic coupling provided by a magnet located on the base in association with a metal plate on the support for the device, or other equivalent means.

While in accordance with the patent statutes a preferred embodiment and best mode has been presented, the scope of the invention is not limited thereto, but rather is measured by the scope of the attached claims.

What is claimed is:

1. A syringe uncapping device comprising:
   two opposed, pivotal gripping arms for engaging a protective syringe needle cap;
   a spring connecting said arms for biasing the arms toward each other;
   a vertically rotatable 360° cam plate located between said arms whose rotation moves said arms alternately toward and away from each other;
   a housing with an opening therein for inserting a hypodermic syringe needle cap;
   said cam plate rotating means comprising:
   a movable plunger shaft having two ends;
   a needle cap contact surface located on one of said ends;
   a cam plate operating lever pivotally attached to the other of said ends;
   cam plate operating lever biasing means for urging said lever into substantial alignment with said plunger shaft;
   mounting means through which said plunger shaft passes, being slidable therein;
   needle cap contact surface biasing means for urging said needle cap contact surface towards said opening;
   wherein when pressure is applied to said needle cap contact surface by a protective syringe needle cap inserted through said opening, said cam plate can be rotated to a first position where said arms grasp said protective syringe needle cap, and when further pressure is applied to said protective syringe needle cap, said cam plate is rotated to a second position where said protective syringe needle cap is released from said arms;
   wherein said cam plate has a plurality of projecting members extending therefrom, and engagement of said projecting members with said cam plate operating lever causes said cam plate to rotate, thereby desirably positioning said gripping arms.

2. A device according to claim 1, in which said cam plate comprises an octagonal plate, alternate, opposite, edges of which have a first length, and opposite, edges adjacent to said alternate edges have a second length.

3. A device according to claim 2, in which said cam plate operating lever has an angled portion projecting from one end thereof.

4. A device according to claim 3, in which said gripping arms have two ends, a pivotal point of attachment to said housing being located on one of said ends, and a surface for gripping said protective syringe needle cap being located on the other of said ends.

5. A device according to claim 4, in which said needle cap contact surface biasing means is a coil spring located about said plunger shaft between said needle cap contact surface and said mounting means.

6. A syringe uncapping device comprising components including: at least two gripping arms for engaging a protective hypodermic syringe needle cap;
   gripping arm biasing means for biasing said gripping arms toward each other;
   camming means for positioning said gripping arms;
   activating assembly means for adjusting said camming means; and
   a housing for said components with an opening therein for inserting a hypodermic syringe needle cap,
   wherein said activating means comprises:
   a movable plunger shaft having two ends;
   a needle cap contact surface located on one of said ends;
   a camming means operating lever located on the other of said ends;
   means for mounting said plunger shaft;
   contact surface biasing means for urging said contact surface toward said opening; said mounting means being connected to said housing, and said activating assembly means being activated by pressure from said needle cap on said contact surface, and
   wherein said camming means comprises a rotatable member with a plurality of projections extending therefrom, the engagement of said projections with said camming means operating lever causing said rotatable member to rotate, thereby desirably positioning said gripping arms.

7. A device according to claim 6, in which said rotatable member comprises an octagonal plate, alternate edges of which have different lengths, and edges opposite each other have the same length.

8. A device according to claim 7, in which said projections are pins that extend substantially perpendicularly from said plate.

9. A device according to claim 6, in which said camming means operating lever has an angled portion projecting from one end thereof.

10. A device according to claim 9, wherein said gripping arm biasing means is a coil spring which connects said arms.

11. A device according to claim 6, wherein said camming means operating lever is pivotally attached to said plunger shaft and urged into a position parallel to said plunger shaft by a spring member positioned parallel and adjacent to said camming means adjusting lever.

12. A syringe uncapping device comprising:
two opposed, pivotal gripping arms for engaging a protective syringe needle cap;
a spring connecting said arms for biasing the arms toward each other;
a rotatable cam plate located between said arms whose rotation moves said arms alternately toward and away from each other;
a housing with an opening therein for inserting a hypodermic syringe needle cap; said cam plate rotating means comprising:
a movable plunger shaft having two ends;
a needle cap contact surface located on one of said ends;
a cam plate operating lever pivotally attached to the other of said ends;
cam plate operating lever biasing means for urging said lever into substantial alignment with said plunger shaft;
mounting means through which said plunger shaft passes, being slidable therein;
needle cap contact surface biasing means for urging said needle cap contact surface toward said opening;
wherein when pressure is applied to said needle cap contact surface by a protective syringe needle cap inserted through said opening, said cam plate can be rotated to a first position where said arms grasp said protective syringe needle cap, and when further pressure is applied to said protective syringe needle cap, said cam plate is rotated to a second position where said protective syringe needle cap is released from said arms, and
wherein said cam plate has a plurality of projecting members extending therefrom, engagement of said projecting members with said cam plate operating lever causing said cam plate to rotate, thereby desirably positioning said gripping arms.

13. A device according to claim 12, in which said cam plate comprises an octagonal plate, alternate, opposite edges of which have a first length, and opposite edges adjacent to said alternate edges have a second length.

14. A device according to claim 13, in which said cam plate operating lever has an angled portion projecting from one end thereof.

15. A device according to claim 14, in which said gripping arms have two ends, a pivotal point of attachment to said housing being located on one of said ends, and a surface for gripping said protective syringe needle cap being located on the other of said ends.

16. A device according to claim 15, in which said needle cap contact surface biasing means is a coil spring located about said plunger shaft between said needle cap contact surface and said mounting means.

* * * * *